United States Patent
Pham et al.

(10) Patent No.: US 8,531,303 B2
(45) Date of Patent: Sep. 10, 2013

(54) METHOD AND INSTALLATION FOR REAL-TIME INSPECTION OF THE QUALITY OF WATER IN A DELIVERY NETWORK

(75) Inventors: Hao-Nhiên Pham, Paris (FR);
Jean-Michel Laine, Ecquevilly (FR);
Roland Kora, Marly le Roi (FR)

(73) Assignee: Suez Environnement (FR)

( * ) Notice: Subject to any disclaimer, the term of this patent is extended or adjusted under 35 U.S.C. 154(b) by 564 days.

(21) Appl. No.: 12/598,519

(22) PCT Filed: Apr. 23, 2008

(86) PCT No.: PCT/FR2008/000581
§ 371 (c)(1),
(2), (4) Date: Feb. 24, 2010

(87) PCT Pub. No.: WO2008/148952
PCT Pub. Date: Dec. 11, 2008

(65) Prior Publication Data
US 2010/0141459 A1 Jun. 10, 2010

(30) Foreign Application Priority Data
May 4, 2007 (FR) .................................... 07 03249

(51) Int. Cl.
*G08B 21/00* (2006.01)
(52) U.S. Cl.
USPC ........................ 340/603; 210/747.5; 134/43
(58) Field of Classification Search
USPC .......... 340/602, 603, 604; 210/747.5, 747.7, 210/170.07, 170.08; 134/43, 109, 111, 113
See application file for complete search history.

(56) References Cited

U.S. PATENT DOCUMENTS

| | | | | |
|---|---|---|---|---|
| 4,562,552 A * | 12/1985 | Miyaoka et al. | | 700/283 |
| 7,124,036 B2 * | 10/2006 | Rigby et al. | | 702/45 |
| 7,201,180 B2 * | 4/2007 | Ephrat et al. | | 137/14 |
| 7,605,485 B2 * | 10/2009 | Pitchford et al. | | 290/43 |
| 8,175,859 B1 * | 5/2012 | Wu et al. | | 703/9 |
| 2002/0130069 A1 | 9/2002 | Moskoff | | |
| 2004/0006513 A1 * | 1/2004 | Wolfe | | 705/22 |
| 2004/0148113 A1 * | 7/2004 | Sage | | 702/51 |
| 2005/0279169 A1 * | 12/2005 | Lander | | 73/592 |

\* cited by examiner

*Primary Examiner* — George Bugg
*Assistant Examiner* — Edny Labbees
(74) *Attorney, Agent, or Firm* — The Belles Group, P.C.

(57) ABSTRACT

Method for inspecting, in real time, the quality of water of a drinking water delivery network comprising, on the one hand, on connections for consumers, consumption meters ($9a$) fitted with remote-reading devices, and, on the other hand, on-line analysers ($10a$) distributed at supervision points on the network in order to measure at least one parameter of water quality. The meters ($9a$) are fitted with remote-reading devices and the consumption data of the various meters ($9a$), and the measurements of the analysers ($10a$) are transmitted to a programmed computing unit (A) with a kinetic model of decrease of the quality parameter in question; the computing unit (A) permanently updates the hydraulic model according to the consumption data received from the meters ($9a$, $9b$ etc.); the computing unit (A) establishes expected estimated values of the concentration in the water of the parameter in question at the various supervision points of the network, and a prewarning system (w) makes a comparison between the estimated values of the quality parameter and the values measured at various points of the network, a warning being triggered when the difference between the measured value and the expected estimated value exceeds a predetermined threshold.

8 Claims, 2 Drawing Sheets

METHOD AND INSTALLATION FOR REAL-TIME INSPECTION OF THE QUALITY OF WATER IN A DELIVERY NETWORK

CROSS REFERENCE TO RELATED APPLICATIONS

This application is a National Phase filing under 35 U.S.C. §371 of PCT/FR2008/000581 filed Apr. 23, 2008, which claims priority to Patent Application No. 0703249, filed in France on May 4, 2007. The entire contents of each of the above-applications are incorporated herein by reference.

The invention relates to a method for monitoring the quality of water in a drinking water delivery network including consumption meters on branch connections to consumers and in-line analyzers for measuring at least one water quality parameter at surveillance points of the network.

Hydraulic models are generally used to evaluate the state of the distribution network in terms of flow rate and pressure. A remote management system gives the open or closed state of valves in the network.

As shown in FIG. 1 of the appended drawings, distribution of drinking water relies on a resource 1 which can be a waterway, for example, or a spring that has been tapped. The resource 1 feeds water to a treatment plant 2 the outlet from which is connected to a pumping installation 3 that sends the water to one or more storage reservoirs 4. The water from the resource is treated in the plant 2, where elements that are undesirable from the point of view of the quality of the drinking water are eliminated. The outlet from a storage reservoir 4 is connected either to pumping means 5 that deliver drinking water or directly by gravity to a meshed distribution network 6 including branch connection points 7 for pipes 8a, 8b, etc. that supply consumers. Each pipe 8a, 8b, etc. is equipped with a respective consumption meter 9a, 9b, etc.

The quality of the water supplied to the consumers downstream of the meters 9a, 9b, etc. is a major concern for water distribution companies.

Water quality parameters such as the chlorine concentration or turbidity change between the outlet from the treatment plant 2 and the consumption meters 9a, 9b, etc. as a function in particular of the geometry of the network, the distance traveled by the water, and the volume and the flow rate of consumption. In-line analyzers 10a, 10b, etc. are sometimes provided at certain monitoring points of the network to measure at least one water quality parameter, in particular the chlorine concentration.

Controlling quality from the treatment plant 2 as far as the reservoir 4 is easy. Moreover the resource 1, the treatment plant 2, the pumping installation 3, the storage reservoir or reservoirs 4, and the pumping means 5 are precisely located and of limited geographical extent and effective surveillance is therefore possible to guard against unauthorized intrusion likely to affect the quality of the water leaving the reservoir 4.

In contrast, in the underground meshed network 6 real-time control of the quality of the water at different locations is difficult. The network 6 is of wide extent and there are numerous water quality deterioration possibilities. Any point of connection to the network can be considered a potential intrusion point for elements that can affect the quality of the water. As a result surveillance of the meshed network 6 of end users to guard against accidental or malicious intrusion is a difficult problem.

It is routine for the quality of the water from a network such as the network 6 to be tested in accordance with statutory surveillance programs involving analysis of a few quality parameters, generally on a daily basis. This low frequency is not compatible with the rapid response required for real time surveillance.

The water quality regulations and increased demand from users have led to water distribution companies installing in-line analyzers, particularly chlorine analyzers for bacteriological quality surveillance. Quality parameters other than chlorine concentration can be taken into account, in particular turbidity. The residual chlorine level in a water distribution network always shows a variation that corresponds to a normal daily evolution depending on the actual consumption of water and the hydraulic state of the network. This results in real difficulty in detecting and establishing an abnormal situation in terms of the chlorine level. The same applies to other water quality parameters. Thus setting a simple and constant threshold for a quality parameter level is not enough to ensure fast and reliable detection of an abnormal situation.

US 2004/0006513 A1 concerns a surveillance system for protecting a water distribution network against biological or chemical contamination. Parameters of the network are monitored, in particular the flow rate, the free chlorine concentration and the turbidity, and the measured values are compared to historic data. Measurements for implementing a distribution strategy are effected at the outlet from the water treatment plant or water tower and in the network. Such measurements produce indications sufficient to monitor a distribution strategy but insufficient to validate an alarm. In particular, a measurement indicating reverse flow does not necessarily signify an abnormality or an intrusion in the network: it may simply be a balancing action between two production sources (for example two water treatment plants or two water towers) in a meshed network.

The primary object of the invention is to provide a method for monitoring in real time the quality of the water in a distribution network which significantly improves the evaluation of the level of a quality parameter of the distributed water at the various consumption points. Another object of the invention is rapid detection of a drop in quality, in particular after an accidental or malicious intrusion into the distribution network.

According to the invention, a method of monitoring the quality of the water of a drinking water distribution network including consumption meters and in-line analyzers at surveillance points of the network for measuring at least one quality parameter of the water, in which method:

measurements from the analyzers are sent to a calculation unit,
  the calculation unit establishes estimated values of the level in the water of the parameter concerned at the various surveillance points in the network, and
  a pre-alarm system compares the estimated values of the quality parameter and the values measured at various points of the network, an alarm being tripped if the difference between a measured value and an estimated value exceeds a predetermined threshold, is characterized in that, for monitoring in real time:

meters equipped with remote meter reading devices are installed on branch connections to consumers,
  consumption data from the various consumer meters is sent to the calculation unit,
  the calculation unit is programmed with a hydraulic model and a kinetic model of the decrease of the quality parameter concerned, and
  the calculation unit continuously updates the hydraulic model according to consumption data received from the consumer meters.

In particular, abnormal chlorine consumption could signify the intrusion of a biological contaminant.

Installing remote meter reading consumption meters enables the consumption metered by each meter to be transmitted, generally by radio, to a remote fixed receiver which collects all the data coming from its environment. This data is then sent to a centralized system that can offer consumers services such as leak detection, jammed meter detection and more frequent meter readings.

Reverse flow information from a meter is advantageously sent to the pre-alarm system and grouped information on reverse flow and quality parameter level are combined to increase the probability of detecting an abnormality in or an intrusion into the network.

According to the invention, a reverse flow measurement from a consumer meter necessarily signifies an intrusion into the network and thus an abnormality and trips an alarm.

Consumption data from the various meters equipped with remote meter reading devices is preferably sent to the calculation unit at least once per hour.

The water quality parameter that is taken into account to monitor the network in real-time can be the chlorine concentration of the water.

According to another possibility, which may be combined with the preceding possibility, the quality parameter is turbidity.

The invention also concerns an installation for implementing the method defined above in a drinking water distribution network that includes consumption meters and in-line analyzers at monitoring points in the network to measure at least one water quality parameter, which installation also includes:

- a calculation unit which is sent measurements from the analyzers and establishes estimated values of the level in the water of the parameter concerned at the various surveillance points in the network, and
- a pre-alarm system that compares the estimated values of the quality parameter and the values measured at various points in the network, an alarm being tripped if the difference between a measured value and an estimated value exceeds a predetermined threshold, which installation is characterized in that, for monitoring in real time:

- the installation includes meters equipped with remote meter reading devices installed on branch connections to consumers,
- consumption data from the various consumer meters is sent to the calculation unit,
- the calculation unit is programmed with a hydraulic model and a kinetic model of the decrease of the quality parameter concerned, and
- the calculation unit continuously updates the hydraulic model according to consumption data received from the consumer meters.

The installation advantageously includes a fixed remote meter reading system which establishes from all the consumption information sent by the meters an estimated instantaneous consumption that is communicated via a link to the calculation unit.

The remote meter reading system can be adapted to signal a reverse flow, reverse flow information being sent over a link to the pre-alarm system.

The installation preferably includes a remote surveillance system which receives information from the analyzers and which sends the calculation unit via a link, after processing it, information on the pressure and flow rate state of the network and via one or more links information on the level of the quality parameter in the water.

Analyzers advantageously measure the chlorine concentration of the water, which constitutes one quality parameter.

Apart from the above features, the invention has a number of other features dealt with more explicitly hereinafter in relation to an embodiment that is described with reference to the appended drawings but is in no way limiting on the invention. In the drawings.

Figure 1:
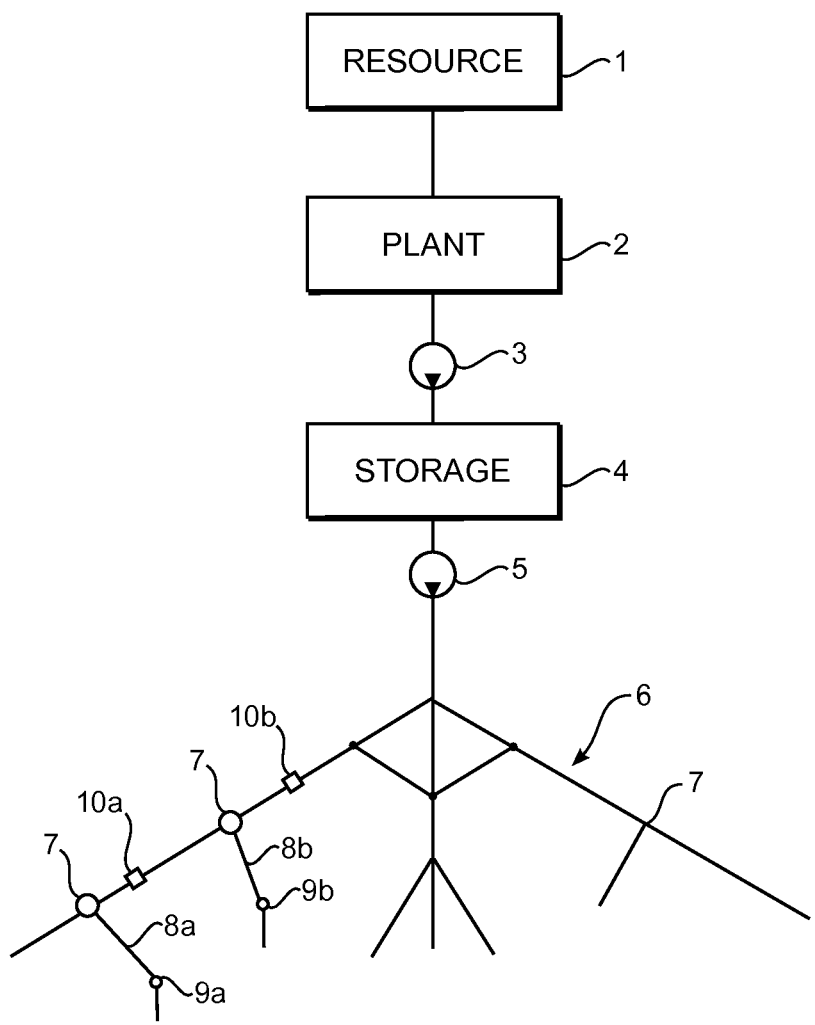
FIG. 1 is a diagram of a water distribution network.
Figure 2:
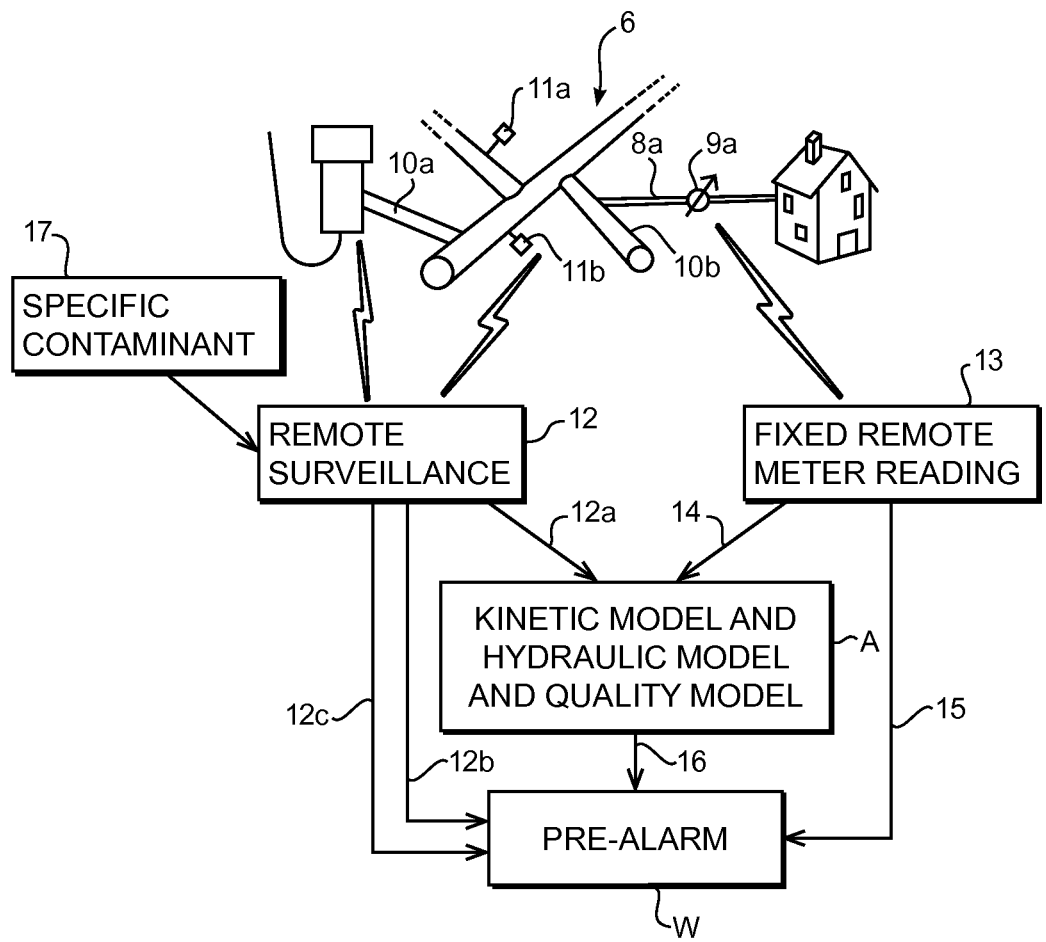
FIG. 2 is a diagram of an installation equipped with a device for implementing the method of the invention.

As shown in FIG. 2, the installation for implementing the method of the invention includes a remote surveillance system 12 which is sent information from analyzers 10a, etc. that measure the level in the water of a quality parameter, in particular the chlorine concentration, and flow rate and pressure information from sensors 11a, 11b, etc. The information is sent by radio and frequently, notably at least hourly.

The installation also includes a fixed system 13 that receives consumption information from the meters 9a, etc. equipped with remote meter reading devices periodically, at least hourly.

The fixed remote meter reading system 13 establishes from all the consumption information sent in by the meters a relatively precise estimate of instantaneous consumption which is communicated over a link 14 to a calculation and processing unit A. A hydraulic model and a quality model are loaded into the unit A.

The fixed remote meter reading system 13 further signals any reverse flow at a meter 9a, etc. which indicates a reduction in consumption instead of an increase. Reverse flow can be caused by accidental or malicious intrusion into the network. The reverse flow information is sent over a link 15 from the system 13 to a pre-alarm system W.

The remote surveillance system 12 sends the calculation unit A via a link 12a information on the state of the pressure and flow rate in the network. Furthermore, the system 12 sends the pre-alarm system W the measured values of the quality parameter or parameters over links 12b, 12c. In the present example, the channel 12b sends the chlorine concentration measurements at the various analysis points of the network and the channel 12c sends turbidity measurements. The calculation unit A is programmed with the hydraulic model and a kinetic model for the decrease in the quality parameter concerned from the outlet of the treatment plant to a point in the network.

The calculation unit A evaluates the level of these quality parameters in the water, in particular the chlorine concentration and turbidity, at various points of the network from information on water consumption, pressure and flow rate in the network and from the levels of the quality parameters measured at the outlet from the treatment plant 2. The pre-alarm system W is provided with this evaluation by a link 16.

It is to be noted that chlorine is consumed continuously in the distributed water because of the possible presence of biological components. Knowing the water consumption figures supplied by the meters 9a, etc. equipped with remote meter reading devices enables precise and reliable prediction of the chlorine concentration of the water, more generally the level of the quality parameter adopted, at the various points of the network.

Information on a specific contaminant can be supplied to the remote surveillance system 12 from a unit 17.

The pre-alarm system W compares the measured values arriving via the links 12b and 12c of the parameters adopted, in particular the chlorine concentration, and the estimated values supplied over the link 16 for the various points at which analyzers are installed. If the difference between a measured value and an expected estimated value exceeds a predetermined limit the system W trips an alarm by any appropriate means.

Because the estimated values take account of consumption and of the natural decrease of the real parameters, a difference between an expected estimated value and a measured value can be attributed with more certainty to an intrusion into the network than if this precise decrease and this precise consumption are not taken into account.

The analysis of reverse flow information supplied over the link 15 constitutes an additional alarm tripping factor.

The chlorine concentration is a very good indicator for tracking water quality. If a biological or chemical intrusion occurs in the network upstream of measurement points equipped with analyzers, it reduces the chlorine concentration at the analyzers near the intrusion. The measured chlorine concentration then becomes significantly less than the estimated concentration calculated and supplied over the link 16 and can be used to trip an alarm.

Sending information on the status of the distribution network makes it possible to determine if valves are open or closed.

The grouped information on reverse flow and on the level of the quality parameter, in particular the chlorine concentration, can be combined to increase the probability of detecting a fault in or intrusion into the network.

According to the invention, surveillance is effected at three levels:
- level 1: measurements at the outlet from the water treatment plant or the water tower for control of reagent doses;
- level 2: measurements effected in the network by analyzers 10*a*, 10*b*, etc. and sensors 11*a*, 11*b*, etc. for implementing a distribution strategy;
- level 3: real-time measurements by the consumer meters 9*a*, 9*b*, etc. for surveillance of the distributed water and very fast alarm tripping.

The method and the installation of the invention enable real-time surveillance of the quality of the distributed water and can be used to detect malicious intrusion corresponding to intentional contamination of the water of the network.

The invention claimed is:

1. A method of monitoring the quality of the water of a drinking water distribution network including consumption meters and in-line analyzers at surveillance points of the network for measuring at least one quality parameter of the water, in which method:
   measurements from the analyzers (10*a*, 10*b*, etc.) are sent to a calculation unit (A),
   the calculation unit (A) establishes estimated values of the level in the water of the parameter concerned at the various surveillance points in the network,
   measured values of the quality parameter at the various points of the network are sent to a pre-alarm system (W), and
   the pre-alarm system (W) compares the estimated values of the quality parameter and the values measured at various points of the network, an alarm being tripped if the difference between a measured value and an estimated value exceeds a predetermined threshold,
   wherein, for monitoring in real time:
   end user meters (9*a*, 9*b*, etc.) equipped with remote meter reading devices are installed on branch connections to end user consumers,
   consumption data from the various end user meters (9*a*, 9*b*, etc.) is sent to the calculation unit (A),
   the calculation unit (A) is programmed with a hydraulic model and a kinetic model of the decrease of the quality parameter concerned,
   using the hydraulic and the kinetic models, the calculation unit (A) evaluates the level of the quality parameter concerned in the water, and
   the calculation unit (A) continuously updates the hydraulic model according to consumption data received from the end user meters (9*a*, 9*b*, etc.),
   wherein reverse flow information from the end user meters (9*a*, 9*b*, etc.) is sent to he pre-alarm system (W) and grouped information on reverse flow and quality parameter levels are combined to increase the probability of detecting an intrusion into the network.

2. The method as claimed in claim 1, wherein consumption data from the end user meters (9*a*, 9*b*, etc.) equipped with remote meter reading devices is sent to the calculation unit (A) at least once per hour.

3. The method as claimed in 1, wherein the water quality parameter taken into account for real time monitoring of the network is the chlorine concentration of the water.

4. The method as claimed in claim 1, wherein the quality parameter is the turbidity.

5. An installation for implementing a method as claimed in claim 1, wherein a drinking water distribution network that includes consumption meters and in-line analyzers at monitoring points in the network to measure at least one water quality parameter, which installation also includes:
   a calculation unit (A) which is sent measurements from the analyzers (10*a*, 10*b*, etc.) and establishes estimated values of the level in the water of the parameter concerned at the various surveillance points in the network, and
   a pre-alarm system (W) which is sent measured values of the quality parameter at the various points of the network and that compares the estimated values of the quality parameter and the values measured at various points in the network, an alarm being tripped if the difference between a measured value and an estimated value exceeds a predetermined threshold,
   wherein, for monitoring, in real time:
   the installation includes end user meters (9*a*, 9*b*, etc.) equipped with remote meter reading devices installed on branch connections to end user consumers,
   consumption data from the various end user meters (9*a*, 9*b*, etc.) is sent to the calculation unit (A),
   the calculation unit (A) is programmed with a hydraulic model and a kinetic model of the decrease of the quality parameter concerned,
   using the hydraulic and the kinetic, models, the calculation unit (A) evaluates the level of the quality parameter concerned in the water, and
   the calculation unit (A) continuously updates the hydraulic model according to consumption data received from the end user meters (9*a*, 9*b*, etc.),
   wherein it includes a fixed remote meter reading system (13) which establishes from all the consumption information sent by the end user meters (9*a*, 9*b*, etc.) an estimated instantaneous consumption that is communicated via a link (14) to the calculation unit (A), and
   wherein the remote meter reading system (13) is adapted to signal a reverse flow from one the end user meters (9*a*, 9*b*, etc.), reverse flow information being sent over a link (15) to the pre-alarm system (W).

6. The installation as claimed in claim 5, wherein it includes a remote surveillance system (12) which receives information from the analyzers (10*a*, 10*b*, etc.) and which sends the calculation unit via a link (12*a*), after processing it, information on the pressure and flow rate state of the network and via one or more links (12b, 12c) information on the level of the quality parameter in the water.

7. The installation as claimed in claim 5, wherein analyzers (10a, 10b, etc.) measure the chlorine concentration of the water, which constitutes one quality parameter.

8. A method of monitoring the quality of the water of a drinking water distribution network including consumption meters and in-line analyzers at surveillance points of the network for measuring at least one quality parameter of the water, in which method:

measurements from the analyzers (10a, 10b, etc.) are sent to a calculation unit (A), the calculation unit (A) establishes estimated values of the level in the water of the parameter concerned at the various surveillance points in the network, measured values of the quality parameter at the various points of the network are sent to a pre-alarm system (W), reverse flow information from end user meters (9a, 9b, etc.) is sent to the pre-alarm system (W), an alarm being tripped when reverse flow is detected, and the pre-alarm system (W) compares the estimated values of the quality parameter and the values measured at various points of the network, an alarm being tripped if the difference between a measured value and an estimated value exceeds a predetermined threshold, wherein, for monitoring in real time:

the end user meters (9a, 9b, etc,) are equipped with remote meter reading devices and are installed on branch connections to end user consumers, consumption data from the end user meters (9a, 9b, etc.) is sent to the calculation unit (A), the calculation unit (A) is programmed with a hydraulic model and a kinetic model of the decrease of the quality parameter concerned, using the hydraulic and the kinetic models, the calculation unit (A) evaluates the level of the quality parameter concerned in the water, and the calculation unit (A) continuously updates the hydraulic model according to consumption data received from the end user meters (9a, 9b, etc.).

* * * * *